(12) United States Patent  (10) Patent No.: US 8,372,156 B2
Holtmann et al.  (45) Date of Patent: Feb. 12, 2013

(54) HIP JOINT SOCKET

(75) Inventors: Miriam Holtmann, Tuningen (DE);
Elke Lohrmann, Cologne (DE)

(73) Assignee: Aesculap AG, Tuttlingen (DE)

( * ) Notice: Subject to any disclaimer, the term of this patent is extended or adjusted under 35 U.S.C. 154(b) by 0 days.

(21) Appl. No.: 13/068,457

(22) Filed: May 10, 2011

(65) Prior Publication Data

US 2011/0282460 A1  Nov. 17, 2011

Related U.S. Application Data

(63) Continuation of application No. PCT/EP2009/062044, filed on Sep. 17, 2009.

(30) Foreign Application Priority Data

Nov. 20, 2008 (DE) .................. 10 2008 058 153

(51) Int. Cl.
*A61F 2/32* (2006.01)

(52) U.S. Cl. ............... 623/22.24; 623/22.19; 623/22.21

(58) Field of Classification Search .... 623/22.11–22.39; A61F 2/32

See application file for complete search history.

(56) References Cited

U.S. PATENT DOCUMENTS

| | | | | |
|---|---|---|---|---|
| 4,731,088 A * | 3/1988 | Collier | .................. | 623/22.13 |
| 4,822,369 A * | 4/1989 | Oueveau et al. | ............ | 623/22.14 |
| 4,936,861 A | 6/1990 | Muller et al. | | |
| 5,263,988 A | 11/1993 | Huebner | | |
| 6,361,565 B1 * | 3/2002 | Bonutti | .................. | 623/22.12 |
| 6,706,071 B1 * | 3/2004 | Wolter | ................. | 623/22.13 |
| 6,761,741 B2 * | 7/2004 | Iesaka | .................. | 623/22.26 |
| 2005/0267585 A1 | 12/2005 | Sidebotham | | |

FOREIGN PATENT DOCUMENTS

| | | |
|---|---|---|
| DE | 30 46 553 | 7/1982 |
| DE | 42 11 346 | 10/1993 |
| EP | 0 313 762 | 5/1989 |
| FR | 2 635 968 | 3/1990 |

* cited by examiner

*Primary Examiner* — Thomas J Sweet
*Assistant Examiner* — Jason-Dennis Stewart
(74) *Attorney, Agent, or Firm* — Lipsitz & McAllister, LLC

(57) ABSTRACT

In order to avoid any metallic wear of the material of the outer shell of a hip joint socket for implantation into the pelvic bone, comprising an outer shell consisting of metal and an insert arranged in it for supporting a joint ball of a femur implant, due to the joint ball sliding past the lower edge of the outer shell it is suggested that the lower edge of the outer shell be covered by a non-metallic material.

6 Claims, 7 Drawing Sheets

HIP JOINT SOCKET

This application is a continuation of international application number PCT/EP2009/062044 filed on Sep. 17, 2009 and claims the benefit of German application number 10 2008 058 153.4 filed on Nov. 20, 2008.

The present disclosure relates to the subject matter disclosed in international application number PCT/EP2009/062044 of Sep. 17, 2009 and German application number 10 2008 058 153.4 of Nov. 20, 2008, which are incorporated herein by reference in their entirety and for all purposes.

BACKGROUND OF THE INVENTION

The invention relates to a hip joint socket for implantation into the pelvic bone, comprising an outer shell consisting of metal and an insert arranged in it for supporting a joint ball of a femur implant.

In the case of provision of a hip endoprosthesis, with which not only a hip joint socket with insert but also a femur implant with stem and joint head are implanted, the joint head is guided along the lower edge of the outer shell during setting or repositioning in a very forceful engagement and this can lead to metal being deposited on the joint ball which the joint ball strips from the edge of the metallic outer shell when sliding over its edge. This can occur, in particular, when the joint ball consists of a very hard material, for example of ceramics or a cobalt-chromium alloy, while the outer shell, as is customary, consists of titanium or a titanium alloy. Layers of titanium then appear on the joint heads following setting and these metallic layers on the joint head can lead to an increased wear of the insert material, with which the joint head interacts in the inserted state.

The object of the invention is to prevent any such metallic layer on the joint ball and, therefore, any increased wear of the insert material caused thereby.

SUMMARY OF THE INVENTION

This object is accomplished in accordance with the invention, in a hip joint socket of the type described at the outset, in that the lower edge of the outer shell is covered by a non-metallic material. This configuration prevents any direct contact of the joint ball with the metallic material of the outer shell during repositioning and it is, therefore, also ensured that no material from the outer shell can be deposited on the joint ball.

It may be provided for the non-metallic material to also extend over the lower end of the insert but this is not absolutely necessary.

The non-metallic material can cover the lower end of the outer shell in different ways.

For example, it may be provided for the non-metallic material to have the form of a film, in particular a film which can be withdrawn from the lower edge of the outer shell and, where applicable, the insert.

In another embodiment, it is provided for the non-metallic material to have the form of a coating of the lower edge of the outer shell and, where applicable, the insert.

In, again, another embodiment, the non-metallic material has the form of an overlay on the lower edge of the outer shell and, where applicable, on the lower edge of the insert.

In this respect, the overlay can be held on the lower edge of the outer shell in different ways, for example, by way of adhesion or, in particular, by means of a clamping connection so that, where applicable, it is also possible to release the overlay from the outer shell after successful repositioning.

In one preferred embodiment, the overlay has a support consisting of metal which is coated with the non-metallic material at its end facing away from the lower edge of the outer shell. The metallic support serves the purpose of connecting the outer shell, on the one hand, and the non-metallic material, on the other hand.

In a further, preferred embodiment, the overlay has the form of a cushion which can be pressed together. This can consist of a uniform, elastically compressible material; in a modified embodiment the cushion has a sheath which is filled with a flowable material.

It may be provided for the non-metallic material to be a material which can be resorbed by the body and so this material will gradually be broken down and eliminated after implantation.

The non-metallic material can be a flowable lubricating material; it is possible to use a tissue adhesive or gelatin as non-metallic material.

The use of a plastic as non-metallic material is particularly advantageous, this plastic being preferably selected from the group of the following materials: polyethylene, polyether ether ketone, polyoxymethylene, polyphenylsulfone, thermoplastic elastomers, polyurethane, polytetrafluoroethylene.

The following description of preferred embodiments of the invention serves to explain the invention in greater detail in conjunction with the drawings.

DETAILED DESCRIPTION OF THE INVENTION

Figure 1:
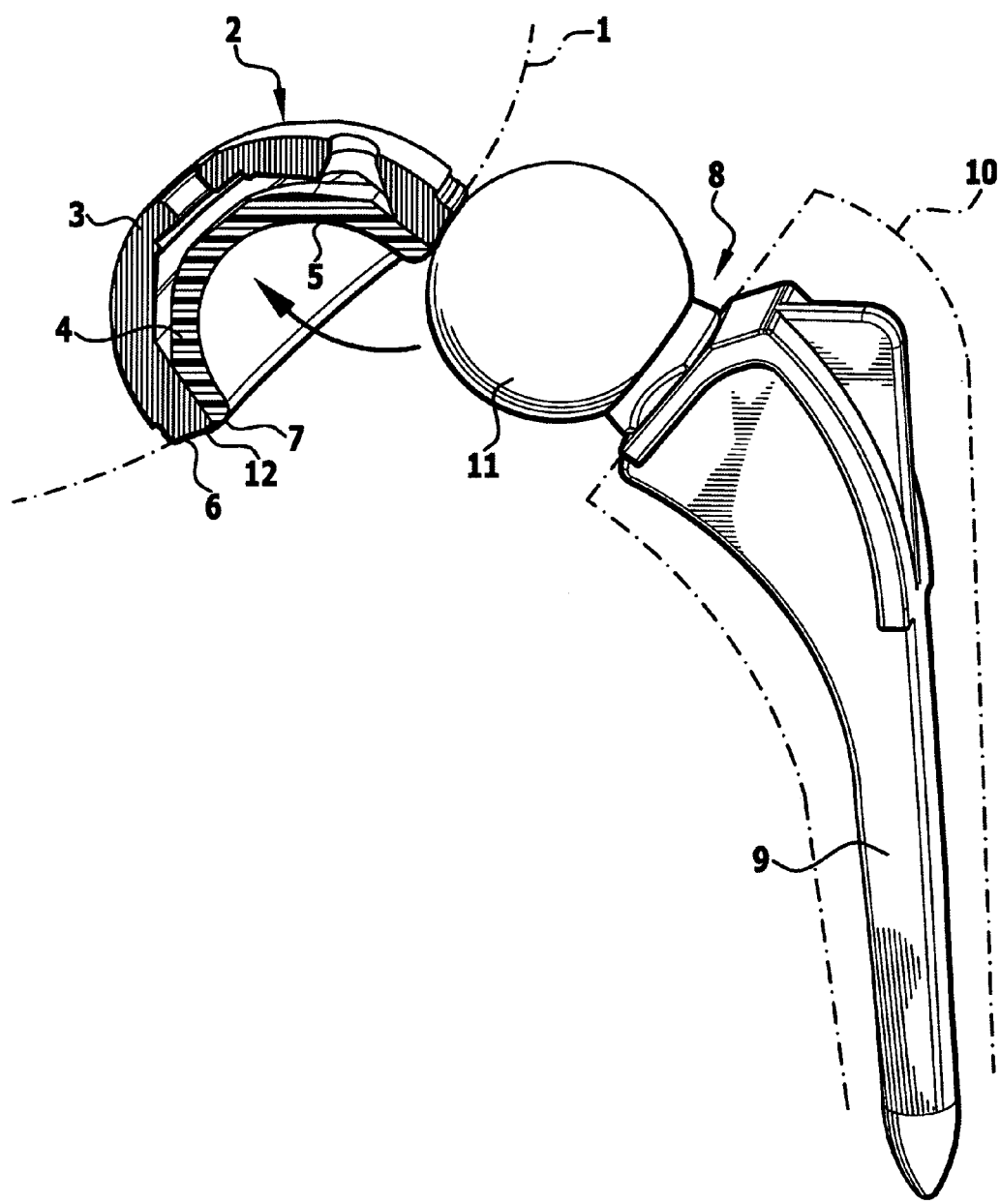
FIG. 1: shows a hip joint socket implanted into a pelvic bone and a femur implant provided with a joint ball during insertion of the joint ball into the insert of the hip joint socket.

A hip joint socket 2 implanted into a pelvic bone 1 is illustrated in FIG. 1 and has a semi-spherical outer shell 3 consisting of metal, for example consisting of titanium or a titanium alloy, into which a shell-shaped insert 4 is inserted which likewise has essentially the shape of a semi-sphere and which forms a semispherical bearing surface 5 on its inner side. At their lower edges, the outer shell and the insert 4 both end in a lower edge 6 and 7, respectively, which are located next to one another.

FIG. 1 also illustrates a femur implant 8 with a stem 9 which is implanted into a femur 10 and which bears a joint ball 11 which is arranged outside the femur 10 and the external diameter of which corresponds to the internal diameter of the bearing surface 5. The femur implant 8 normally consists of metal, for example, of a cobalt-chromium alloy but can also consist of ceramics.

After the hip joint socket 2 has been implanted in the pelvic bone 1 and the femur implant 8 in the femur 10, the joint ball must be positioned in the bearing surface 5 and, for this purpose, it is necessary to push the joint ball 11 past the lower edge 6 of the outer shell 3 and also the lower edge 7 of the insert 4, as is apparent from the illustration of FIG. 1. On account of the considerable forces of the ligamentous apparatus, the joint ball 11 and the lower edges 6, 7 of the outer shell and the insert 4, respectively, are pressed forcefully against one another.

In order to avoid the joint ball 11 coming into contact with the metallic material of the outer shell 3 and taking along material from it, the lower edge 6 of the outer shell 3 and, where applicable, also the lower edge 7 of the insert 4 are covered by a non-metallic material. This prevents the direct contact of the joint ball with the metallic material of the outer shell 3 and, therefore, protects not only the lower edges of the outer shell 3 and the insert 4 but also the joint ball 11 from undesired damage.

Very different possibilities are available for the design of this cover.

Figure 2:
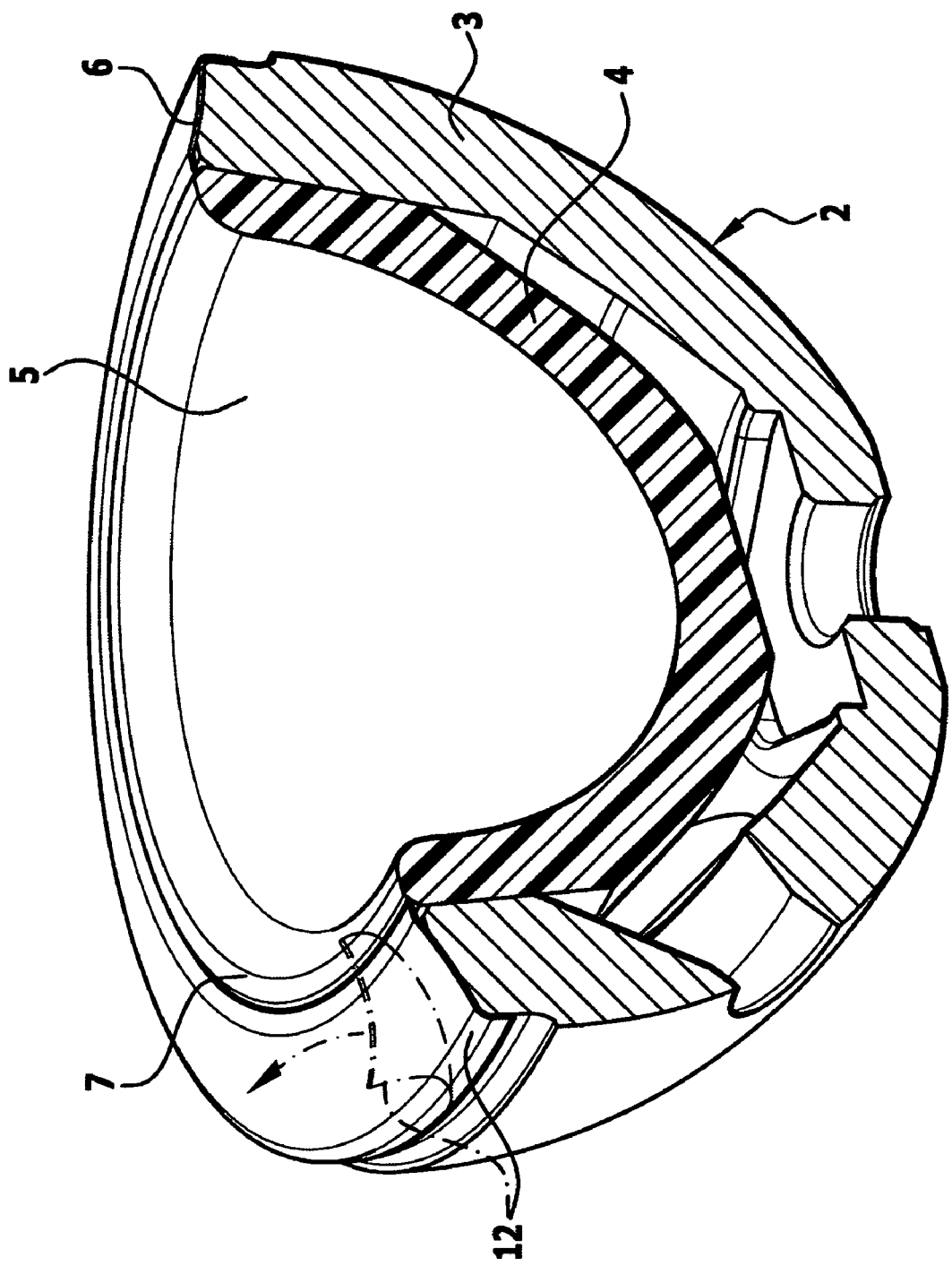
FIG. 2: shows a perspective view of a hip joint socket illustrated in cross section with a covering of the lower edge of the outer shell in the form of a removable film.

In the embodiment of FIG. 2, the lower edge 6 of the outer shell 3 is covered by a removable film 12; this can be secured to the lower edge 6 with the aid of an adhesive or, however, also on account of attraction forces between the film 12, on the one hand, and the lower edge 6, on the other hand. After the joint ball 11 has been set in the bearing surface 5, this annular film can be withdrawn from the lower edge 6.

Figure 3:
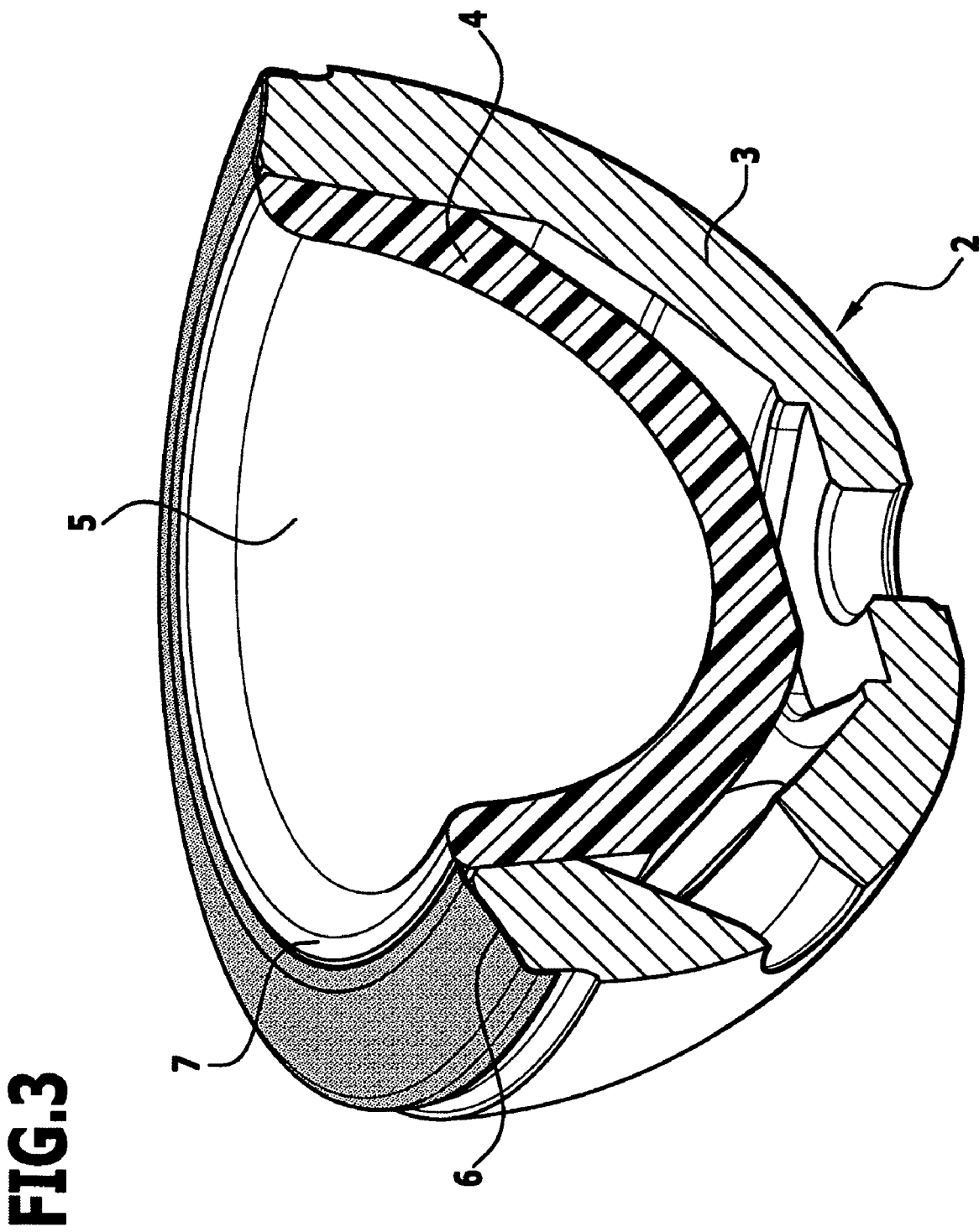
FIG. 3: shows a view similar to FIG. 2 with a coating of the lower edge of the outer shell by means of a tissue adhesive.
Figure 4:
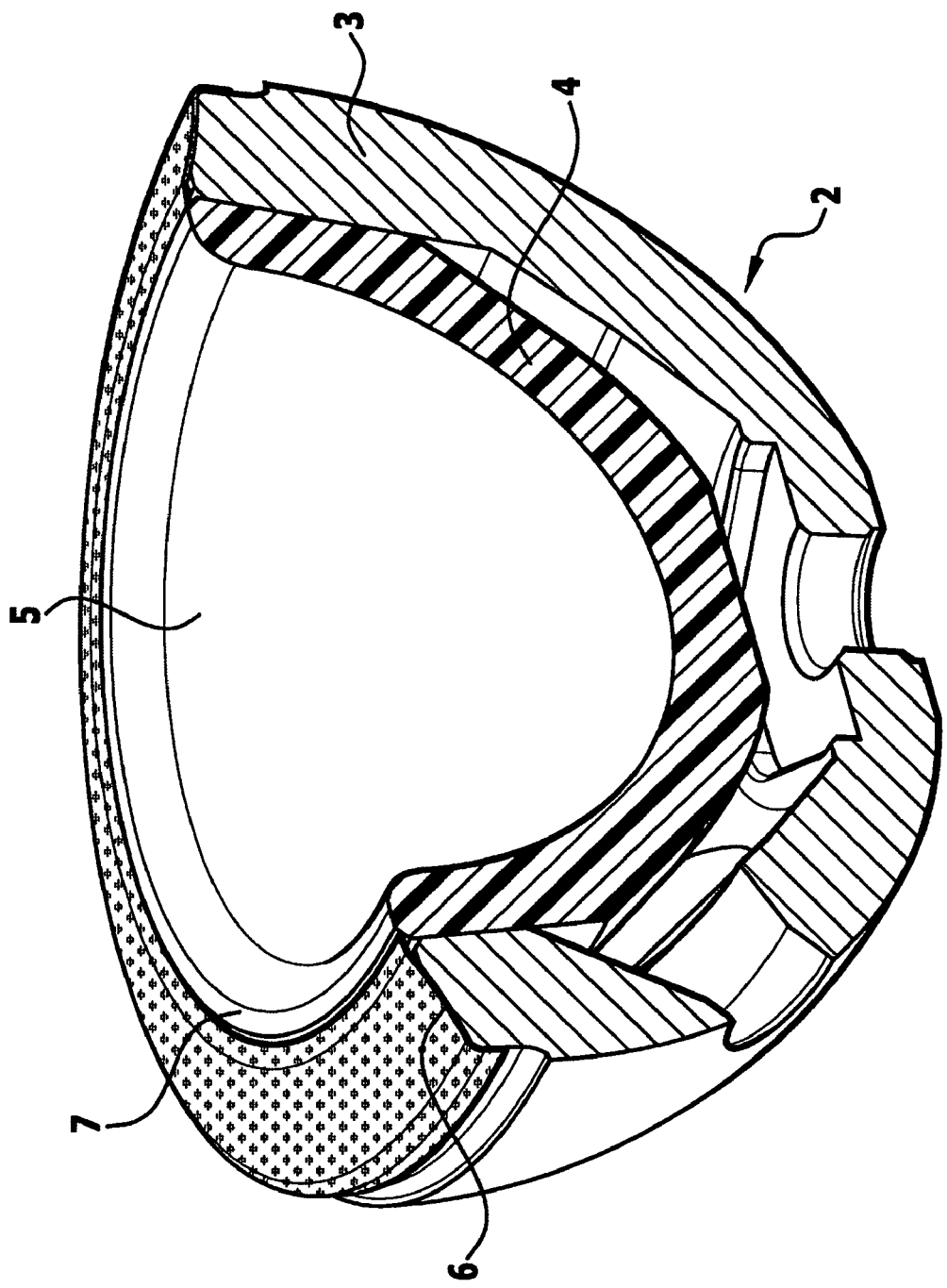
FIG. 4: shows a view similar to FIG. 3 with a coating consisting of gelatin.

It is also possible, as illustrated in FIG. 3, to coat the lower edge 6 with a non-metallic substance, for example by means of a biocompatible lubricating material, such as, for example, silicon oil or viscous gelatin, as illustrated in FIG. 3, or by means of gelatin, as illustrated in FIG. 4. These materials can preferably be resorbed by the body and so they are gradually degraded and resorbed following a successful implantation.

Figure 5:
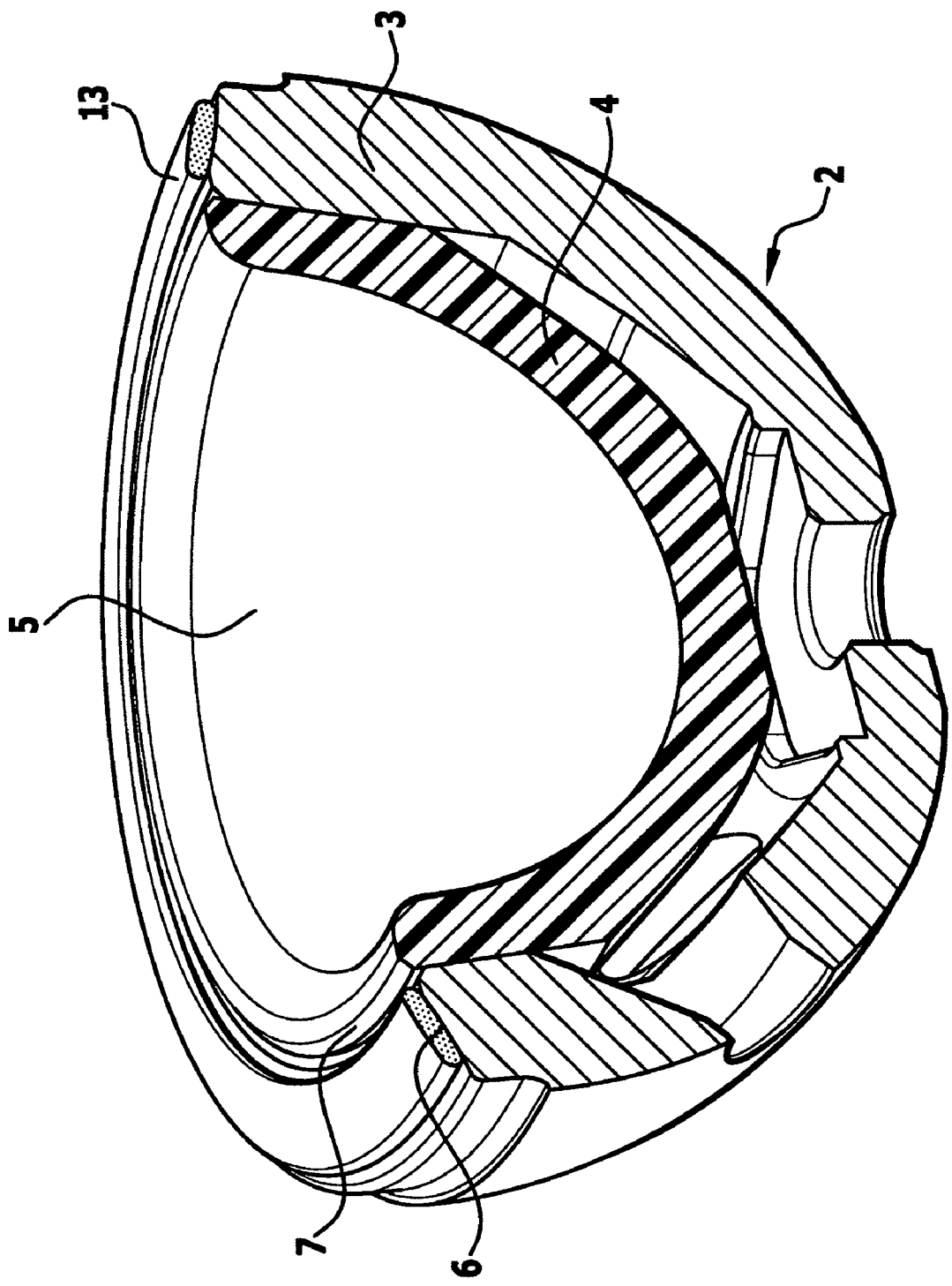
FIG. 5: shows a view similar to FIG. 2 with a covering of the lower edge of the outer shell in the form of an annular cushion.

In the embodiment of FIG. 5, an annular cushion 13 is placed on the lower edge 6 and this can consist of a compressible material, for example, consisting of a hydrogel, of silicon or of a thermoplastic elastomer; it is also possible for this cushion 13 to have an outer sheath which is filled with a flowable material, for example a NaCl solution. This cushion 13 can also be held releasably on the lower edge 4.

Figure 6:
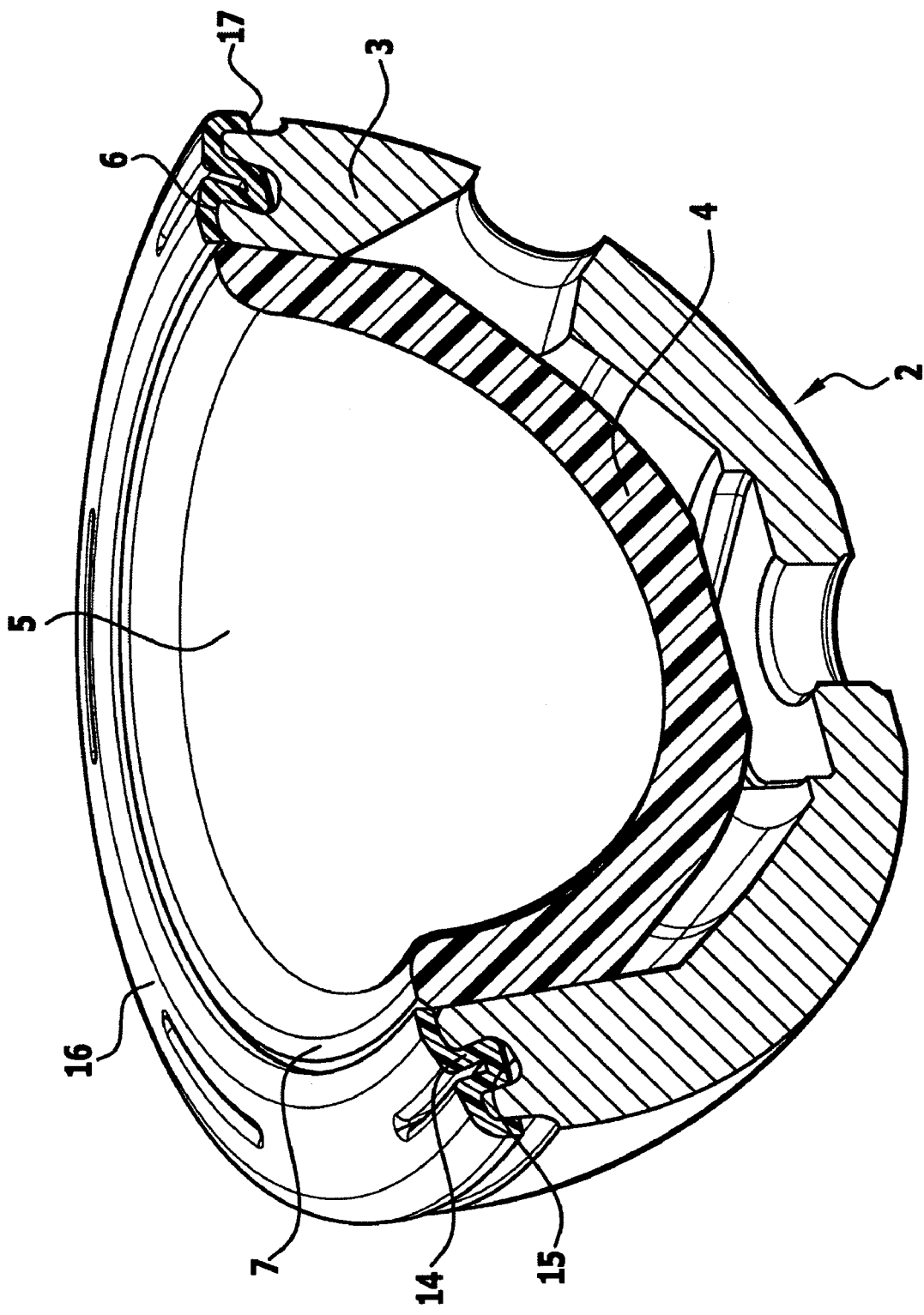
FIG. 6: shows a view similar to FIG. 2 with a covering of the lower edge of the outer shell in the form of a plastic ring held in a clamping fit on the outer shell

In the embodiment of FIG. 6, a plastic ring 16 is placed on the lower edge 6 so as to cover it and this is secured in a clamping manner to the lower edge 6 by means of several clip projections 14; these clip projections 14 dip into recesses 15 in the lower edge 6. The clamping action is reinforced, in addition, by edges 17 of the plastic ring 16 which are bent over at the side and engage around the lower edge 6 of the outer shell 3.

This plastic ring 15 can also, where applicable, be removed from the outer shell 3 by releasing the clamping connection but it is also possible for this plastic ring 16 to remain following implantation; it can, in particular, consist of a resorbable plastic material which will gradually be decomposed and degraded by the body.

Possible materials for such a plastic ring 16 are, for example, polyethylene, polyether ether ketone, polyoxymethylene, polyphenylsulfone, thermoplastic elastomers, polyurethane or polytetrafluoroethylene.

Figure 7:
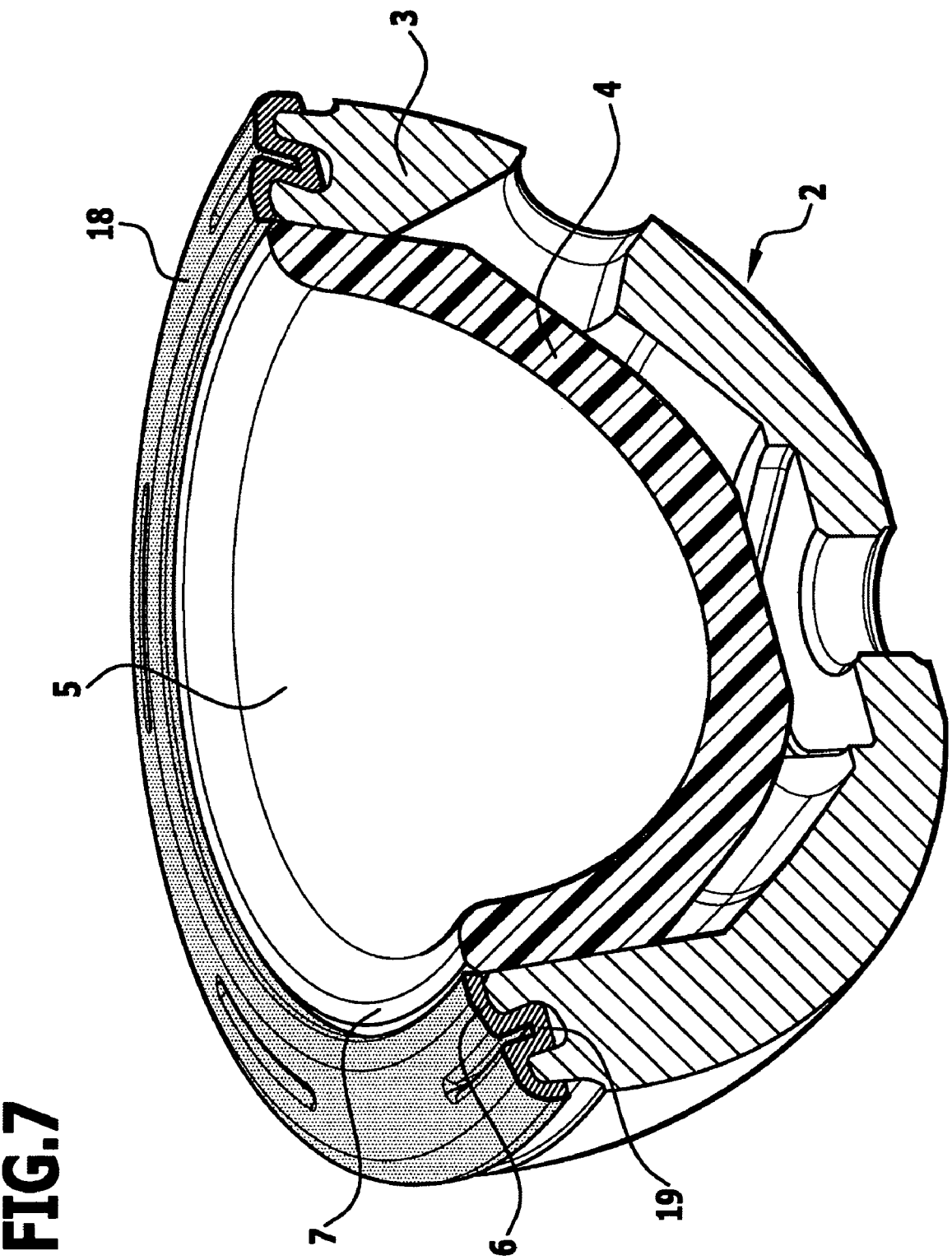
FIG. 7: shows a view similar to FIG. 6 with a cover ring for the lower edge of the outer shell with a metallic support coated in plastic.

Whereas, in the embodiment of FIG. 6, the covering is brought about by a ring which consists completely of plastic, a cover ring 18 of a similar shape is provided for the covering in the embodiment of FIG. 7 and this consists of a metallic support 19 and is coated with a plastic material on its side facing away from the outer shell 3. This material can consist of the same plastic materials as those mentioned above.

The invention claimed is:

1. Hip joint socket for implantation into the pelvic bone, comprising:
   an outer shell consisting of metal, and
   an insert arranged in the outer shell for supporting a joint ball of a femur implant, a lower edge of the outer shell being covered by a non-metallic material,
   wherein:
      the non-metallic material has the form of a coating which adheres to the lower edge of the outer shell, and
      the non-metallic material is a material resorbable by the body.

2. Hip joint socket as defined in claim 1, wherein the coating of the non-metallic material also extends over a lower edge of the insert.

3. Hip joint socket as defined in claim 2, wherein the non-metallic material is a tissue adhesive.

4. Hip joint socket as defined in claim 1, wherein the non-metallic material is a tissue adhesive.

5. Hip joint socket for implantation into the pelvic bone, comprising:
   an outer shell consisting of metal, and
   an insert arranged in the outer shell for supporting a joint ball of a femur implant, a lower edge of the outer shell being covered by a non-metallic material,
   wherein:
      the non-metallic material has the form of a coating which adheres to the lower edge of the outer shell, and
      the non-metallic material is a tissue adhesive.

6. Hip joint socket for implantation into the pelvic bone, comprising:
   an outer shell consisting of metal, and
   an insert arranged in the outer shell for supporting a joint ball of a femur implant, a lower edge of the outer shell being covered by a non-metallic material,
   wherein:
      the non-metallic material has the form of a coating which adheres to the lower edge of the outer shell, and
      the non-metallic material is gelatin.

\* \* \* \* \*